United States Patent [19]

Young et al.

[11] Patent Number: 5,182,513
[45] Date of Patent: Jan. 26, 1993

[54] METHOD AND APPARATUS FOR A MULTI-CHANNEL MULTI-FREQUENCY DATA ACQUISITION SYSTEM FOR NONDESTRUCTIVE EDDY CURRENT INSPECTION TESTING

[75] Inventors: John D. Young, Rexford; Kristina H. Hedengren, Schenectady; Donna C. Hurley, Albany, all of N.Y.

[73] Assignee: General Electric Company, Schenectady, N.Y.

[21] Appl. No.: 696,456

[22] Filed: Apr. 6, 1991

[51] Int. Cl.$^5$ .................. G01N 27/72; G01N 27/82; G01R 33/12
[52] U.S. Cl. .............................. 324/232; 324/233; 324/242
[58] Field of Search ............. 324/232, 233, 239, 240, 324/241, 242, 243, 262

[56] References Cited

U.S. PATENT DOCUMENTS

| | | | |
|---|---|---|---|
| 4,303,885 | 12/1981 | Davis et al. | 324/232 |
| 4,965,519 | 10/1990 | Tornblom | 324/225 |
| 5,047,719 | 9/1991 | Johnson et al. | 324/242 |

FOREIGN PATENT DOCUMENTS

673896 4/1990 Switzerland ................. 324/242

OTHER PUBLICATIONS

"Eddy Current Imaging for Defect Characterization," D. C. Copley, GE/Aircraft Engines, Evendale, OH, Review of Progress in Quantitative Nondestructive Evaluation, vol. 2B, Plenum Press, New York, 1983, pp. 1527-1540.

"Eddy Current Imaging," R. O. McCary, D. W. Oliver, K. H. Silverstein, and J. D. Young, IEEE Transactions on Magnetics, vol. MAG-20, No. 5, Sep. 1984, pp. 1986-1988.

"Eddy Current Imaging of Surface-Breaking Structures," R. E. Joynson, R. O. McCary, D. W. Oliver, K. H. Silverstein-Hedengren, L. L. Thumhart, GE/CR&D, Schenectady, NY, IEEE Transactions on Magnetics, vol. MAG-22, No. 5, Sep. 1986, pp. 1260-1262.

"Eddy Current Printed Circuit Probe Array: Phase IIA," T. G. Kincaid, Signametrics Report No. 10, Dec. 29, 1988 (Appeared in GE Final Report No. 2880582Y20XG, Eddy Current Technology Improvement, Jan. 1989 as an appendix).

"Automating an Eddy Current Test System for In-Service Inspection of Turbine/Generator Rotor Bores," R. O. McCary and J. R. M. Viertl, GE/CR&D and GE/Power Generation, Schenectady, NY, IEEE Transactions on Magnetics, vol. 24, No. 6 Nov. 1988, pp. 2594-2596.

"Use of Imaging Techniques for Eddy Current NDE," K. H. Hedengren, R. O. McCary and J. D. Young,

(List continued on next page.)

*Primary Examiner*—Walter E. Snow
*Attorney, Agent, or Firm*—James R. McDaniel; Paul R. Webb, II

[57] ABSTRACT

The invention discloses an inspection system for detecting near surface flaws or defects in conductors using nondestructive eddy current testing suitable for industrial application. The system provides a method and apparatus for acquiring real time, synchronized, discrete eddy current measurement signals from a plurality of sufficiently disposed, spatially correlated eddy current probes then processing and formatting said measurement signals automatically over parallel data channels to accommodate digital processing techniques in order to produce on eddy current image. Utilizing digital image processing provides a capability for improving flaw detection limits while simultaneously enhancing image resolution.

12 Claims, 7 Drawing Sheets

OTHER PUBLICATIONS

GE/CR&D, Schenectady, NY, Review of Progress in Quantitative Nondestructive Evaluation, vol. 7A, edited by D. O. Thompson and D. E. Chimenti (Plenum Publishing Corp., 1988), pp. 357–365.

"Flexible Substrate Eddy Current Coil Arrays," Y. D. Krampfner and D. D. Johnson, Review of Progress in Quantitative Nondestructive Evaluation, vol. 7A, pp. 471–478, 1988.

"Eddy Current Probe Evaluation: Experimental Measurements & System Interaction," K. H. Hedengren, R. O. McCary and J. D. Young, GE/CR&D, Schenectady, NY, Review of Progress in Quantitative Nondestructive Evaluation, vol. 8A, edited by D. O. Thompson and D. E. Chimenti, (Plenum Publishing Corp., 1989).

"Eddy Current Image Processing for Crack Size Characterization," R. O. McCary, GE/CR&D, Schenectady, NY, Review of Progress in Quantitative Nondestructive Evaluation, vol. 8A, edited by D. O. Thompson and D. E. Chimenti, Plenum Press, New York, 1990, pp. 773–780.

"Eddy Current Printed Circuit Probe Array: Phase I," T. G. Kincaid, Signametrics Report No. 9, Sep. 12, 1987 (also appeared as an appendix to a GE Final Report).

METHOD AND APPARATUS FOR A MULTI-CHANNEL MULTI-FREQUENCY DATA ACQUISITION SYSTEM FOR NONDESTRUCTIVE EDDY CURRENT INSPECTION TESTING

RELATED APPLICATIONS

The present application is related to U.S. patent application Ser. No. 07/696,455, entitled "Eddy Current Probe Arrays" by Kristina H. Hedengren et al, which discloses and claims a probe array herein considered the preferred embodiment of the present application Application Ser. No. 07/696,457, entitled "Multi-frequency Eddy Current Sensing" by Kristina H. Hedengren, discloses and claims a method of operation for improving resolution and characterization in nondestructive eddy current flaw detection. Both referenced applications are assigned to the same assignee as the present application and are filed concurrently herewith being incorporated herein by reference in their entireties.

Application Ser. No. 07/504,769 entitled "A Flexible High Density Interconnect Structure and Flexibly Interconnected System" by Charles W. Eichelberger, et al describes a multi-layer, multi-component integrated fabrication technology suitable for making flexible, spatially correlated, miniature probe arrays for inspecting difficult surface geometries. This co-pending application is assigned to the same assignee as the present application and is incorporated herein by reference in its entirety; although, it is not filed concurrently herewith.

BACKGROUND

The present invention relates to a method and apparatus for inspecting conductive surfaces for small near surface fatigue cracks or flaws in an in-service or production line environment. To accommodate stringent inspection requirements, e.g. government safety specification tolerances on aircraft engines, the inspection system must be capable of detecting and characterizing flaws heretofore undetectable by conventional techniques. Image processing techniques have long been employed in visual, X-ray and ultrasound inspection systems but are not commonly applied to eddy current nondestructive testing (NDT).

One method of eddy current NDT uses a probe comprising two separate coils operating in reflectance mode. If the eddy current probe contains two separate coils, drive coil and sense coil, it is said to be operating in reflectance mode. If the probe drive coil surrounds two sense coils connected in series and both sense coils are on the conductor surface it is said to be operating in differential mode. If one sense coil is on the conductor surface and the other sense coil is on a fixed reference (conductor or air) the probe is operating as an absolute, probe. The advantage of using probes operating in reflectance mode is that drive and sense signals on respective coils are easily separable, whereas in differential probes they are not due to a bridge circuit mode of detection. Operation of the reflectance mode probe involves measuring the voltage difference at a sense coil when it is excited by a frequency driven alternating current flowing in a nearby drive coil. The potential difference of the sense coil changes near the surface of a conductor as currents are induced to flow in the conductor in response to the magnetic flux generated by alternating currents flowing through the drive coil. As the drive coil is brought near the surface of a conductor, current will be induced in the conductor near the surface and will remain under the probe as it is moved across the surface. The voltage measured will be approximately constant until a near surface fatigue crack or flaw is encountered. At that time, the induced current flow is disrupted or deflected and the measured impedance changes. This disruption is measured as a change in sense coil voltage indicative of the flaw signal measured by a reflectance mode eddy current probe.

Typical eddy current probes employed for NDT in the industrial inspection of conductive parts use inductive coil elements wound around ferrite cores to intensify induced magnetic flux. The coil winding radius onto the ferrite core presents a limit on the flaw size that can be detected. Inspection is usually accomplished by having an individual split core differential probe traverse the surface of the conductor in a repeat pattern to adequately scan the surface area of the conductive part under inspection. Conventional flaw detection is accomplished by monitoring the sense coil response signal of a single scanning probe to detect a voltage disruption threshold over noise for that probe. The smaller the flaw, the harder it becomes to distinguish flaw signal from background noise. Prior art monitoring for occurrences of such single threshold phenomenon using single probe inspection scanning is time and labor intensive and not conducive to image processing of automatically acquired measurement signals. Spatially correlated measurements can be obtained from this type of single probe traverse scanning wherein time histories along the scan path are retained and used for imaging. Flaw detection often involves looking for the recurrence of a difficult to distinguish threshold flaw signal that might otherwise be considered as noise. The use of imaging techniques as applied to eddy current Non-Destructive Testing (NDT) was first suggested by D. Copley, Review of Progress in Quantitative Nondestructive Evaluation, Vol. 2B, Plenum Press New York, 1983, p. 1527. Copley introduced imaging based on asynchronously acquiring one dimensional signals for two dimensional formatting without any refinement. Imaging in this manner is accomplished by indexing signal intensity as measured at predetermined positions along the scan path to an ordered two dimensional array to provide crude spatial correlation of asynchronous measurements. The problem with this imaging approach is that it is time and labor intensive. Furthermore, imaging is spatially blurred due to the much larger relative size of the probe compared to the flaw. This masks refinement efforts, making it difficult to interpret underlying defects.

SUMMARY OF THE INVENTION

An object of this invention is to provide a method and apparatus for quickly acquiring a plurality of spatially correlated, real time eddy current measurements and formatting these measurements for automated image processing.

Another object of this invention is to provide inherently spatially correlated, synchronous, discrete measurement signals simultaneously acquired from a measurement array of sufficiently distributed eddy current probes designed to accommodate nondestructive eddy current inspection of conductive surfaces.

Yet another object of the invention is to provide an adequate single scan capability by triggering temporally correlated automatic measurement collection for the plurality of spatially correlated probes comprising the array.

A further object of the invention is to format discrete eddy current probe measurement signals for parallel processing.

A still further object of the invention is to provide a reference frequency phase adjustment for each measurement signal.

Yet another object of the invention is to provide channel multiplexing capability for driving each probe of the array and/or demodulating corresponding responsive measurement signals.

A further object of the invention is to provide tuning capability for driving probes at multiple frequencies in order to meet changing detection and resolution sensitivity requirements.

A final object of the invention is to speed up the inspection process while improving accuracy and reliability.

The present invention is generally directed to a new method and apparatus for industrial nondestructive flaw detection using an improved eddy current inspection system for acquiring and formatting signals for better flaw imaging. The invention is more particularly directed to providing an image processing capability through systematic acquisition of synchronously collected, spatially correlated discrete eddy current measurement signals obtained in a temporally and spatially synchronized manner for image processing; said system being capable of simultaneously improving detection sensitivity and inspection productivity. Measurements are made using a surface scanning measurement array comprising a plurality of sufficiently distributed eddy current probes disposed to accommodate the surface of a conductor in an industrial inspection environment. The plurality of measurement signals is simultaneously obtained in a precision manner from a single scan using a synchronized trigger sampling method. The signal acquisition system is capable of automatically acquiring eddy current probe measurements from each of the plurality of probes and formatting each for parallel image processing via independent multiple channels which may be multiplexed. The inspection system phase demodulates all probe measurement signals into complex sinusoidal component pairs and provides a capability for multiplexing the demodulation process. In the case of a spatially correlated probe array, phase demodulation of the entire phase correlated array is accomplished by demodulating a single probe measurement. The system is further capable of simultaneously driving each of the plurality of probes at select multiple frequencies in an independent or demultiplexed manner. Multiple data acquisition channels provide a capability for faster flaw detection and multiple frequencies improve flaw characterization. Multi-frequency driving provides excitation as well as reference phase adjustment for each of the plurality of probe measurement signals while simultaneously providing a tuning capability to refine image resolution sensitivity for detection of flaw signals heretofore undetectable by conventional means.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings in which:

DETAILED DESCRIPTION OF THE INVENTION

Figure 1:
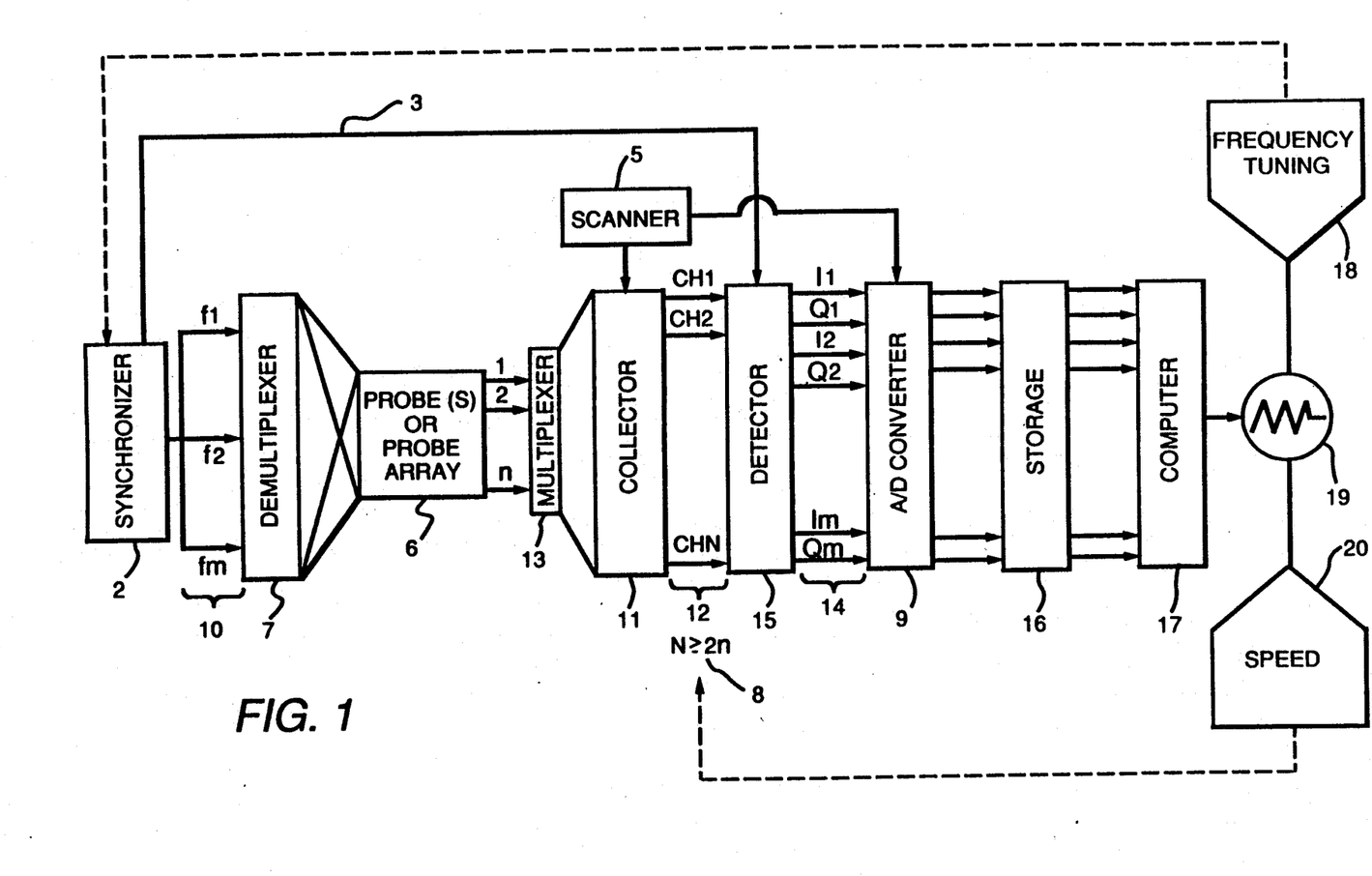
FIG. 1 is a simplified schematic of a multi-frequency, multi-channel eddy current inspection system or apparatus.

In FIG. 1, a multi-frequency, multi-channel eddy current inspection system and apparatus is shown which has an automatically controlled frequency synchronizer 2 operating to drive the system. Measurement scanning modes typically employ single or multiple measurement probe(s) or a probe array wherein measurements are collected using a mechanical scanner or a spatially correlated measurement array of probes. Probe(s) 6 operating in a given scanning mode are driven by single or multiple frequencies 10 which are shown as f or $f_1, f_2, \ldots f_m$, generated by the synchronizer 2. Single or multiple frequencies 10 excite each of the plurality of measurement probes 6. Multiple frequence excitation can occur simultaneously using a demultiplexing means 7. In such case, each frequency of the multiplicity of frequencies 10 drives each probe of the plurality of probes 6. Each responsive probe measurement signal is collected, via synchronous collection means 11, and multiplexed, via multiplexing means 13, to independent parallel data channels 12. Data collection proceeds using automatic scanning means 5 cooperating in conjunction with the probe configuration being used to scan the plurality of probes for signal collection via collection means 11. The measurement signals, for the case of a probe array, are inherently spatially correlated. Measurements are collected on independent data channels 12 which are shown as CH1, CH2... CHN. Discrete measurement signals are independently collected and each is input to a demodulating synchronous detector 15 to obtain a pair of demodulated basis signals 14 for each measurement signal of the plurality. This is accomplished by phase adjusting each signal against an appropriate reference signal 3 generated by the frequency synchronizer 2. Each probe's basis measurement signal pair 14 consists of a complex sinusoidal in phase (I) and quadrature phase (Q) component. For n probes, the number of data channels required corresponds to at least twice the number of measurement probes; i.e. N=2n independent data channels are required as indicated at 8 in the figure. Image processing requires isolation of each probe's I and Q measurement components among the N independent channels identified at 14 for each driving frequency 10. Each component is formatted for digital processing using an analog to digital converter 9. Digitizing cooperates with scanning means 5 to synchronize and correlate data collection. Thereupon the digitally converted component signal is stored for processing via appropriate storage means 16. Each signal component is formatted and available to undergo parallel image processing by an automated computational device, such as a computer, 17 in order to produce an image on a display means 19 of a detected flaw. The detection and analysis of the image of a surface fatigue crack or flaw using eddy current NDT data obtained by driving the multi-channel system with multiple frequencies provides improved flaw detection and characterization, including a multi-resolution frequency tuning 18, which allows probe sensitivity to be tuned via proper choice of drive frequencies. The parallel image processing of each probe measurement signal, collected simultaneously from a multiplicity of probes, on independent data channels enhances flaw detection and increases productivity. Thus, increasing the number of independent channels can provide a speed adjustment; as can providing a plurality of probes for data collection. This increased speed feature is identified at 20.

An eddy current probe consists of at least two mutual induction coil elements electrically coupled through the conductive inspection surface. The drive coil is connected to an oscillating source establishing that element as a driver coupled to remaining sense element(s). A plurality of such probe(s) 6 are sufficiently disposed to provide simultaneous, discrete, measurement signals for synchronous collection 11 but suitable choice of scanning means 5. A probe array 6 simultaneously provides spatial correlation for the measurement signals. A preferred embodiment for such a probe array is described in detail in concurrently filed application Ser. No. 07/696,455, entitled "Eddy Current Probe Arrays" by Kristina H. Hedengren et al. Briefly, a flexible, multilayer, multicomponent precise fabrication technique is employed to make a plurality of like, miniaturized eddy current coil elements sufficiently distributed to adequately scan a conductive surface in a single scan. In addition, the precise, like, miniaturized, metallized coils are deposited between multiple, flexible, planar layers of substrate and dielectric and interconnected therethrough using General Electric's High Density Interconnect (HDI) processing in order to fabricate an integrated eddy current probe array having a novel flexible support structure. A probe array so constructed conforms to easily accommodate geometrically difficult inspection surfaces.

Figure 2:
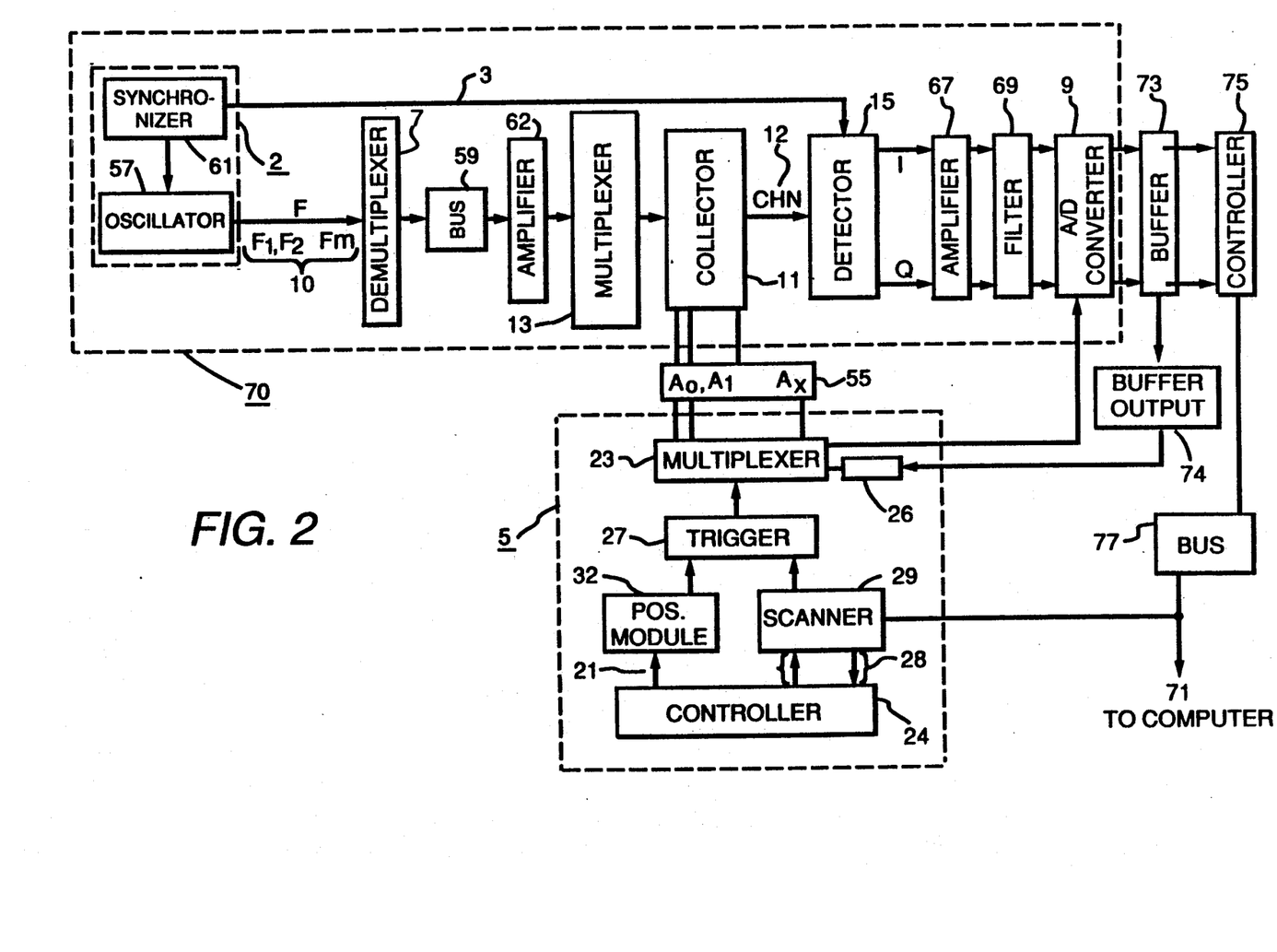
FIG. 2 is a flow diagram illustrating detail of the multi-frequency, multi-channel eddy current inspection system showing an automatic scanning feature cooperating to acquire correlated data from an arbitrary reflection mode eddy current probe.

FIG. 2 shows an automatic scanning data acquisition system for a single arbitrary channel, CHN at 12. The outlined portion identified by numeral 70 accomplishes the same processing discussed generally in FIG. 1; but for a single channel, CHN. The common identification numerals have been preserved wherever possible. System components are modular and assembled into a rack or crate. The modular components are in concept similar to those of the General Electric Company's ECOM 1500 CAMAC system. The scanning system, identified collectively by numeral 5, is designed to be versatile. The system of components described herein is comprised of CAMAC modular electronics controlled by a Microvax VMS computer 71. Details of the computer are not disclosed in FIG. 2 as other computational devices are included within the scope of the present invention. Communication control with computer 71 is provided by a Kinetic Systems KS3989 communications controller 75 operating in conjunction with a Motorola VME data bus 77. Scan control 5 is accomplished using an Anorad Axis controller 24, a digital counter circuit 26 to generate multiplexer addresses 55 which are shown as A0, A1...Ax, an analog to digital trigger 27 and a digital multiplexer 23 coupled to a suitable mechanical scanning mechanism. For instance, flat plates can be continuously scanned under the direction of a programmable pulse on position module 32. Means for axial scanning 29 is employed when the geometry to be scanned has an axis of translational symmetry such that all data can be collected in a single scan by one translation of a suitable probe array along the axis of translational symmetry. Axial scanning can be stepped 28 by indexing sensed interval movement along the probe array to the Anorad axis controller 24, or accomplished in a continuous manner by connecting an axial encoder 21 to the pulse on position module 32 to continuously coordinate probe array motion with data collection via addresses identified at 55.

Using buffer transistor components (not shown) with a continuous wave oscillator 57, the probe array is driven by frequency synchronizer 61 which selectively drives a plurality of probes at a single frequency or independently drives each probe of the plurality at a different frequency. If connected in series, as in a probe array, the probes can be driven collectively at multiple frequencies. Frequency driving options are identified by numeral 10. The programmable frequency synchronizer 61 provides not only the probe drive 57 but a precise reference frequency 3 against which a synchronous detector 15 can demodulate a basis component pair from each measured probe signal. The frequency synchronizer 61 has a programmable frequency range of 100 kHz to 20 MHz with a resolution of 0.012 Hz. Its phase range is 0 to 360 degrees with a resolution of 0.09 degrees. The synchronous detector 15 receives the reference frequency 3 from the frequency synchronozer 61 and adjusts its paths to determine how much of the measured signal is in phase with the reference signal. The signal's demodulated basis components, I and Q, identified at 14, pass from the synchronous detector 15 to an amplifier 67 whose gain is 50 dB, then into a low pass filter 69 having a fixed filter bandwidth of 4 kHz and a selectble bandwidth from 10 Hz to 2.56 kHz. The reciprocal band width of the low pass filter 69 determines the minimum multiplexing time of the system. A typical low pass filter bandwidth of 1 kHz permits a multiplexing time of 2 milliseconds which reduces the input noise from 39.6 microvolts to 0.28 microvolts. An Analog to Digital Converter (ADC) 9 digitizes the synchronous detector output 14 in 2 micorseconds and transfers data to a buffer memory 73. The buffer memory strobe output 74 clocks a digital counter 26 to advance the next address 55 at which the video multiplexer 11 will collect data. This retriggers the ADC 9 sequence which was started by the synchronized trigger 27 from scanning mechanism 5. Direct Memory Address (DMA) communication with the CAMAC Motorola VME bus 77 is provided to transfer to disk storage (see 16 of FIG. 1) each channel's data when buffer memory 73 becomes half full while multiplexed data continues to be stored in the top half.

Figure 3:
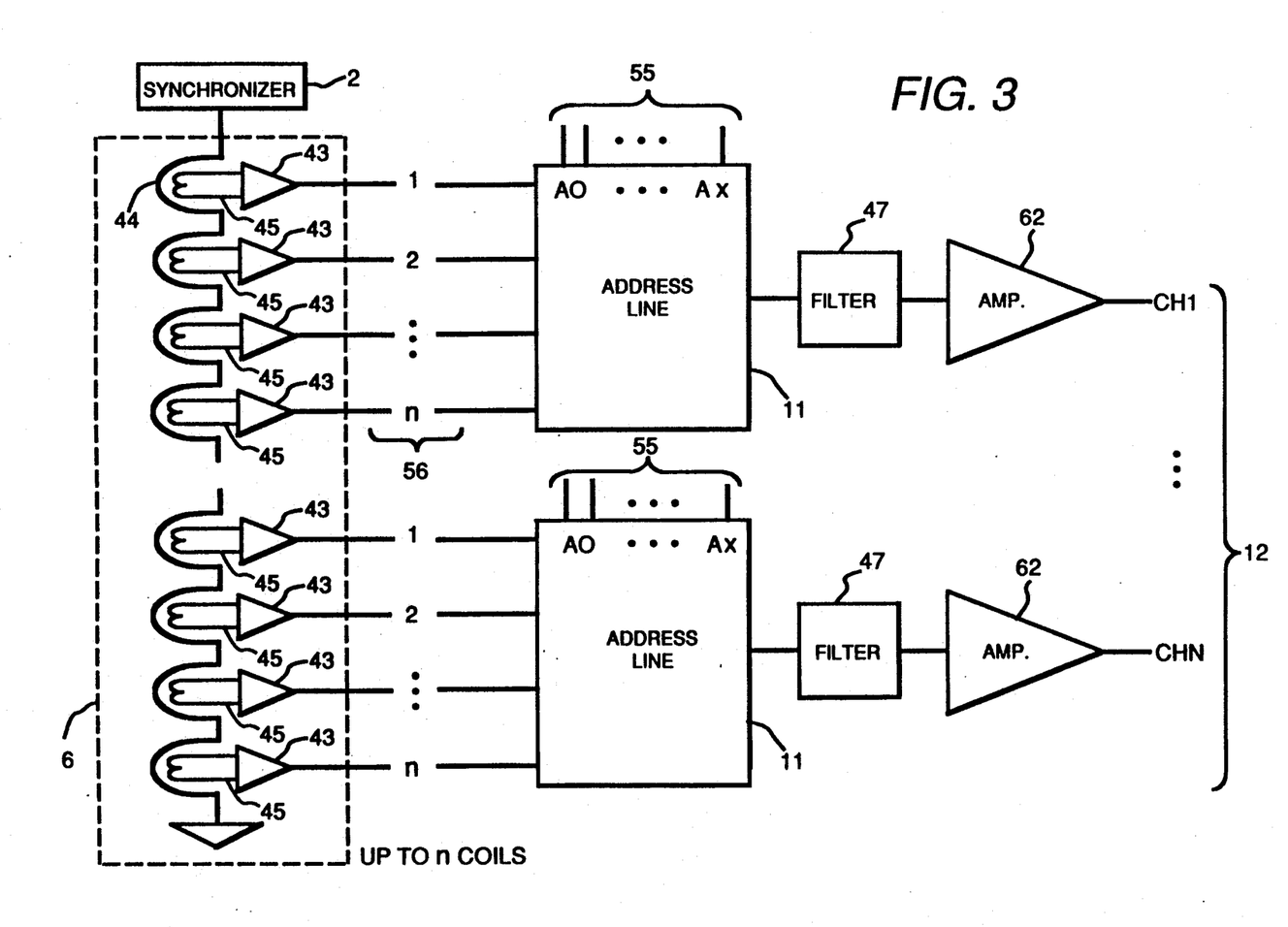
FIG. 3 is a schematic view of an array comprising a plurality of eddy current probes operating in reflection mode to accomplish discrete multi-channel data acquisition.

Data collection is based on a probe array analog multiplexing design illustrated in FIG. 3. Because reflection mode probes have distinct and separable drive, 44 and sense, 45 signals, probe coil elements of the array are preferably configured in reflection mode. Thus, drive coils when series connected, can be collectively driven using automatically controlled frequency synchronizer 2 and buffer transistor components (not shown) with a continuous wave oscillator 57 rather than demultiplexing the individual multi-frequency drives onto independent drive coils of the array. This configurational benefit dismisses issues of unwanted coupling into the highly sensitive input amplifiers 43 which may arise relating to large current switch transients and time constant problems otherwise unavoidable in different array probe element configurations. In FIG. 3 an arbitrary number or sense array elements, herein taken to be n, 56, undergo multiplexing after preamplification using a NE592H video amplifier 43 with individual gain resistor trimmed to 40 dB +0.19 dB −0.08 dB. A video multiplexer 11 available from Analog Devices AD9300KQ, with an analog input of +or −2 volts, a multiplexing settling time of 70 nanoseconds and a channel to channel isolation of 80 dB is used herein. This analog multiplexer is controlled by address lines 55 which as was shown in FIGS. 1 and 2, to control data collection and trigger analog to digital data conversion at 9. The invention contemplates that software could provide many of these functions as well. Filter 47 is an optimum, flat, low-pass LC filter with a −3 dB cutoff frequency of 23 MHz. Line drive amplifier 62 is a Comlinear CLC400AJP which can easily drive up to 30 feet of 50 ohm TRIAX cable 51. TRIAX cable provides necessary shielding to isolate low amplitude, high frequency signals from external interference. A predetermined number, n, of array sense elements are responsively multiplexed after amplification onto select, available, independent shielded cable channels 12. Every channel's video multiplexer address lines 55 are connected together. When interrogation of the analog video multiplexer's address lines 55 so indicates each channel's respective sense element is connected to the line driver amplifier 62 via multiplexer 11 until measurement signals from all n probe elements are collected. Given N available channels 12, multiplexing can accommodate up to nN probe elements.

FIGS. 4–7 describe various modes of operation of the system and system components as described in FIGS. 1–3. Common reference numerals have been preserved where possible. The portion of FIG. 2 identified by numeral 70 provides the framework apparatus upon which the operational discussions of FIGS. 4–7 are based. The reader is referred to U.S. patent application Ser. No. 07/696,457, filed concurrently herewith, for a detailed discussion of operationally tailoring the resolution sensitivity of the herein disclosed and claimed eddy current inspection system through design of probe(s) and multi-frequency operation. System capabilities which support this feature will be operationally discussed in the following.

Figure 4:
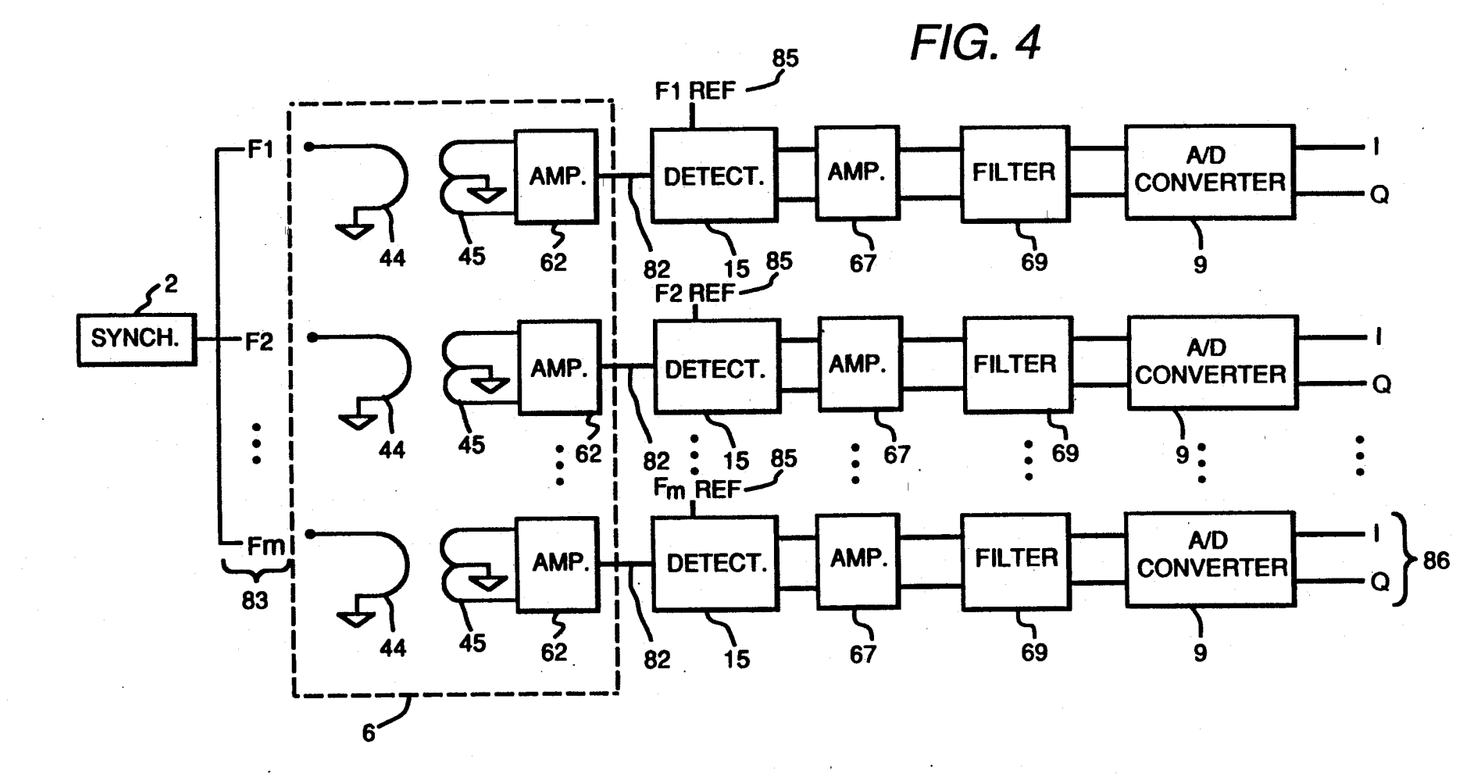
FIG. 4 is a schematic view of operational interconnections for driving a plurality of independent eddy current reflection probes at independent multiple frequencies.

In FIG. 4 an automatically controlled frequency driver 2 drives the drive coil 44 of each of a plurality of independent eddy current reflection probes. Driving occurs at multiple frequencies, $F_1, F_2, \ldots F_m$, as indicated at 83. These driving frequencies may be chosen, as a matter of design, to be the same or different. It can be seen that processing for each independent channel proceeds as indicated within the dotted enclosure identified by numeral 70 in FIG. 2 for an arbitrary multiplicity of probes, herein taken to be given by the integer n. Driving the multiplicity of probes with the same frequency, $F_1=F_2 \ldots =F_m$, provides faster data collection due to simultaneous multiple formation of the same image based on measurements from n different spatially correlated measurement points which are processed over N independent channels; thereby, increasing inspection productivity. Driving the plurality of probes with different frequencies $F_1, F_2, \ldots F_m$, provides for simultaneous formation of m separate images which can be perfectly registered by proper delays. By proper frequency choice, using multi-frequency driving, an operator can tailor sensitivity to various depths with probes of varying dimensional sensitivity to accommodate varying detection requirements. A reference frequency 85 substantially the same as the driving frequency is provided for synchronous detector demodulation by component 15 of each respective independent amplified probe signal 82 into resolved components, I and Q, which after further amplification by 67, filtering by 69 and analog to digital conversion by 9 are shown indicated by numeral 86. The invention disclosed herein contemplates demultiplexing multiple drive frequencies onto a plurality of probe drive coils, the nth drive coil indicated at 44. This offers the option of not only increasing the surface area covered by each frequency, but simultaneously using multi-frequency driving over the plurality of probes to have the widest range of surface geometrical compensation or flaw depth sizing. Using a demultiplexed configuration it becomes more convenient to phase adjust against only one reference frequency; although, phase adjusting against different multiple reference frequencies is within the scope of this invention as well. Though not illustrated in FIG. 4, a sense signal can be multiplexed over the number of available independent channels 12 onto corresponding synchronous detectors, representatively identified at 15, for demodulation against a single reference frequency or against a corresponding multiplicity of reference frequencies.

Figure 5:
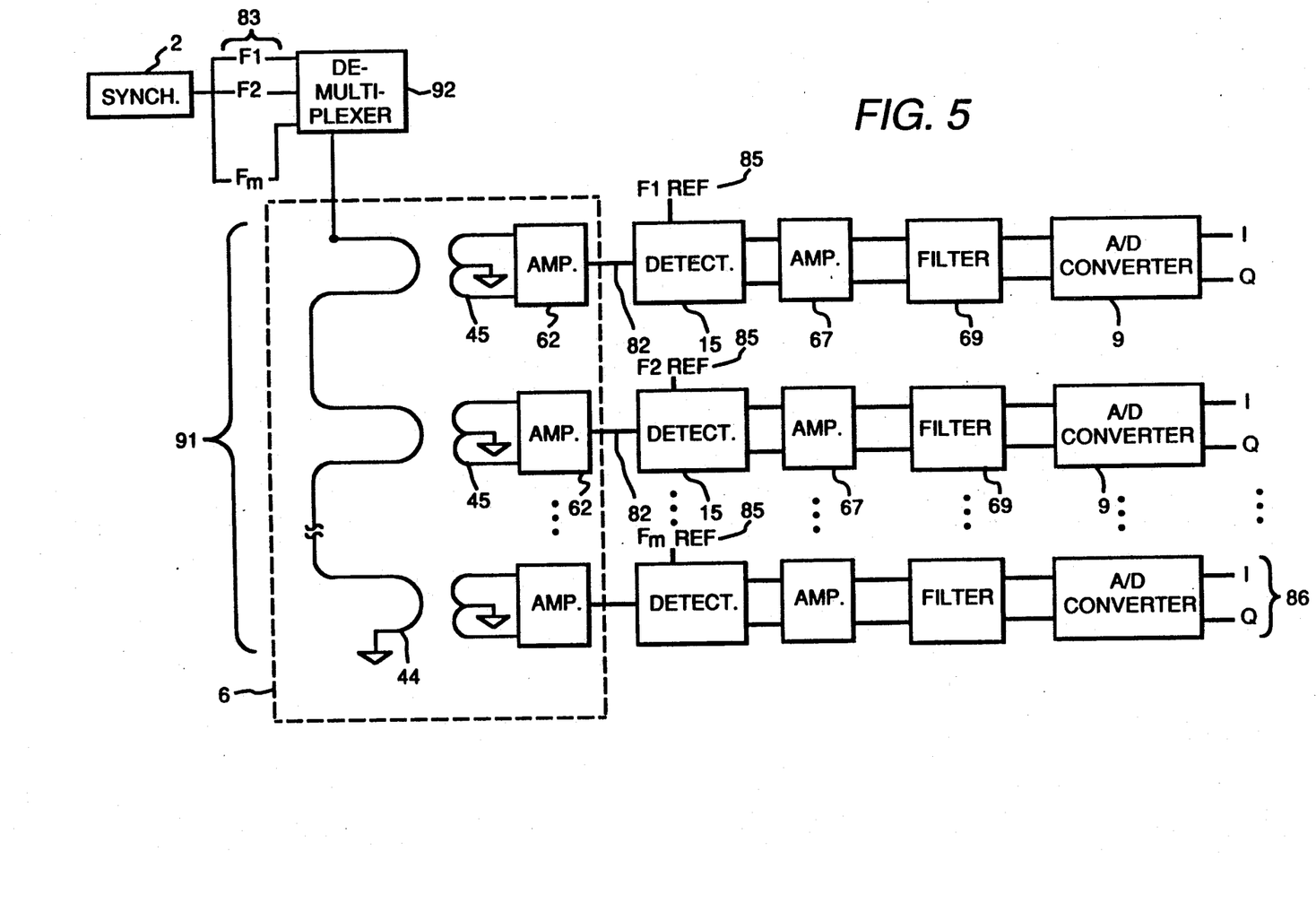
FIG. 5 is a schematic view of operational interconnections for driving a probe array with demultiplexed, i.e. summed, multiple frequencies.

In FIG. 5 multiple frequencies 83 are selectively demultiplexed via a suitable means 92 onto a plurality of drive coils connected in series 91. These changes in interconnection are appended to a configuration basically like that disclosed in FIG. 4 where elements are labelled accordingly. The configuration of FIG. 5 is suited to driving a spatially correlated probe array wherein the connected drive coils of each array element are alternately driven by different (or like) multiple frequencies. Reference frequencies 95 may be different or the same.

Figure 6:
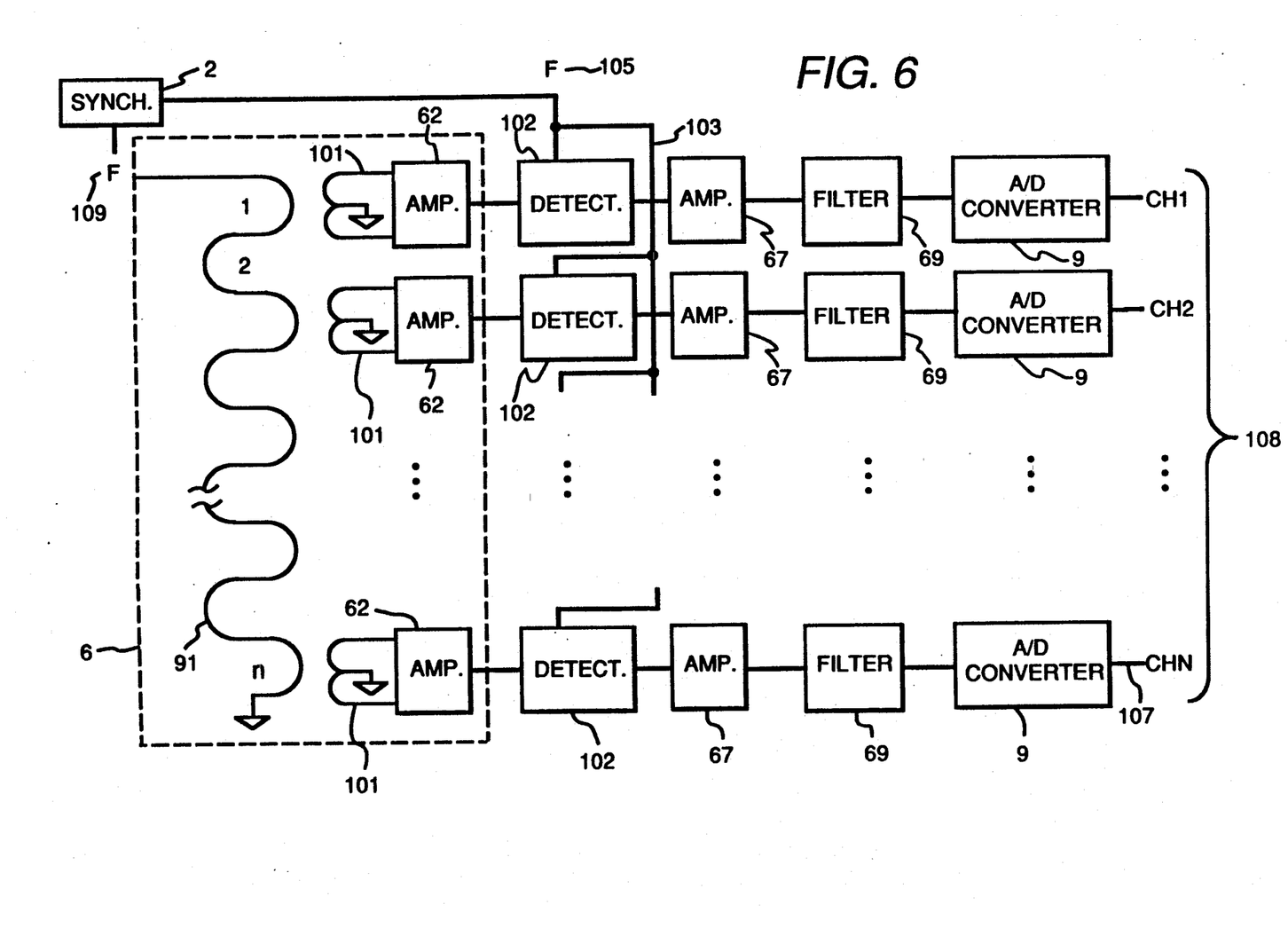
FIG. 6 is a schematic depiction of operational phase demodulation of a frequency driven probe array using a single reference frequency.

FIG. 6 better illustrates operational interconnections for a spatially correlated eddy current probe array. This figure shows differential interconnection of the sense reflection coils 101 differentially using connection means identified at 103 during demodulation by the synchronous detector 102. Due to the differential connection phase adjustment occurs against only a single reference frequency, 105 which is shown as F. However; the phase adjustment can be demodulated against different reference frequencies. A single frequency phase adjustment can demodulate the entire probe array, since the phase relationship of a spatially correlated probe array is predetermined. Therefore, knowing the demodulation phase adjustment for just one signal allows the phase adjustment for the other probes to be determined. For convenience a frequency producing maximum signal output 107 is herein identified among probe signals and chosen for referencing phase adjustment in the remaining probes. Probe signals of the N channels 108 must be interrogated to determine the maximum signal. Such probe signals are obtained after signal processing by amplifier 67, filter 69 and analog to digital converter 9. FIG. 6 illustrates a single frequency 109 driven array 91; although multiple frequencies can be demultiplexed onto the series connected reflector probe drive coils 91 (as in FIG. 5). Frequency driving, in either an independent or demultiplexed manner can be employed for a plurality of independent reflector probe drive coils 44 (as in FIG. 4).

Figure 7:
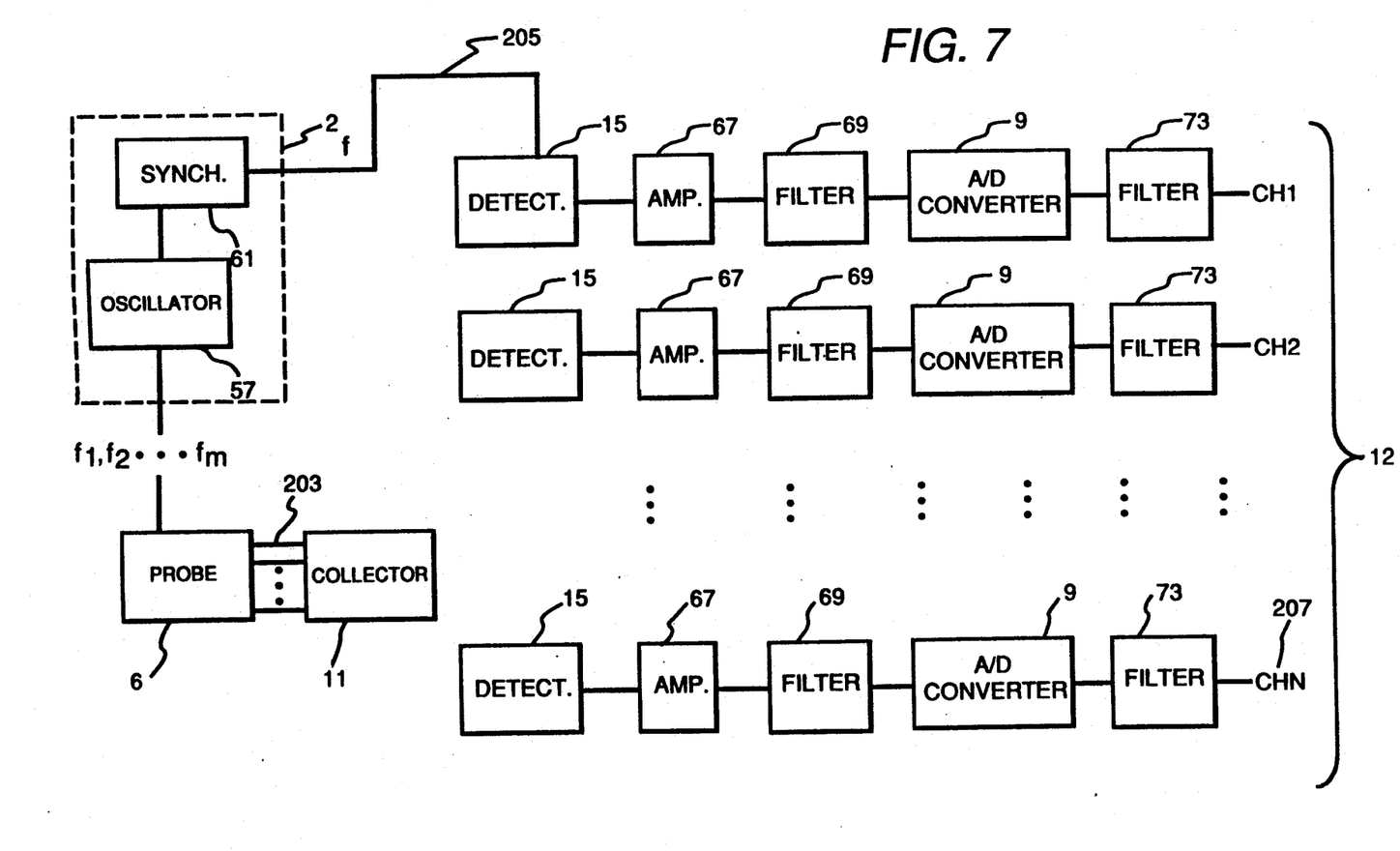
FIG. 7 is a schematic view of the operational interconnections of FIG. 6 for a multiple frequency driven probe array with multiplexed demodulation.

FIG. 7 appends to the configuration of FIG. 6 a means for multiplexing to multiple independent channels 12, using an analog multiplexer 11, to alternately input each pre-amplified drive coil signal 203 from each probe of a reflection coil array 6 for demodulation at 15 against a single reference frequency 205 chosen to maximize signal output from among independent probe signals like that identified at 207 for the array. FIG. 7 best illustrates operational interconnections for a spatially correlated eddy current probe array 6.

The operational discussions presented herein describe the manner in which the multi-frequency, multi-channel eddy current inspection system drives a plurality of eddy current probes with multiple frequencies in an independent or demultiplexed fashion. Responsive signals from the plurality of probes are automatically scanned for data collection and multiplexed onto an available number of independent data channels to facilitate parallel processing. Parallel processing initiates with reference frequency demodulation of each probe signal into two complex sinusoidal components, an in-phase (I) component signal and quadrature phase(Q) component signal. An automated scanning mechanism controls which of the signals collected will e digitized by the along to digital converter. After appropriate signal processing (consisting of amplification, filtering, etc.) and formatting (digitizing) retained signal components are stored for delayed automated image processing or undergo real time automated image processing. The multi-frequency driving feature of the system introduces a multi-resolution capability which improves image diagnostic quality over that presently available by permitting an inspection operator to frequency tune the system to accommodate various flaw detection and characterization requirements. This is accomplished by varying the sensitivities of the probes through selective multiple frequency driving, in effect "tuning" the image using a 'coarse' and 'fine' adjust approach. Multi-frequency driving at the same frequency also acts to speed up image formation. At the same time and with the same system, the utilization of multiple independent data channel processing has not only made it possible to take advantage of those refinements offered by image processing techniques, but inspection scanning is accomplished faster and more accurately. For example; when the system is used in conjunction with single scan probe arrays, data collection speed is improved, thus increasing inspection productivity. Furthermore, when the system is used with a flexible, precise, miniaturized, probe array the system maximizes resolution sensitivity and speed in inspecting even difficult surface geometries for conductors which cannot be inspected by conventional techniques.

While a specific embodiment of the invention has been illustrated and described herein, it is realized that numerous modifications and changes will occur to those skilled in the art. It is therefore to be understood that the appended claims are intended to cover all such modifications and changes as fall within the true spirit and scope of the invention.

We claim:

1. An eddy current inspection apparatus for detecting flaws in a conductive surface comprising:
   a plurality of spatially correlated eddy current probe means;
   means for driving select probe means of the plurality with a plurality of select frequencies;
   means for automatically scanning in a vicinity of the surface to synchronously acquire discrete scan responsive measurement signals from each of the plurality of probe means;
   means for responsively multiplexing each measurement signal onto a predetermined number of independent data channels in order to collect a corresponding plurality of measurement signals for parallel processing;
   means for demodulating each measurement signal of the plurality against a reference frequency in order to obtain a corresponding pair of basis components for image processing;
   means for converting each component pair into digital format;
   automated means for storing the digitized components; and
   means for automated parallel image processing of the digital components.

2. Apparatus according to claim 1 wherein means for providing plural frequency drives to the probe means are the same means for multiplexing probe means signals.

3. Apparatus according to claim 1 wherein the means for driving further comprising means for demultiplexing a plurality of frequencies onto a plurality of probe means.

4. Apparatus according to claim 1 wherein said plurality of probe means are sufficiently disposed to accommodate inspection of said surface in a single scan.

5. Apparatus according to claim 1 wherein said plurality of probe means comprise a spatially correlated array.

6. Apparatus according to claim 1 wherein the scanning means further comprises a means to responsively control scanning to collect measurements.

7. An eddy current inspection apparatus for detecting flaws in a conductive surface comprising:
   a plurality of spatially correlated eddy current probes comprising at least one drive element in cooperation with a plurality of sense elements operating in reflectance mode;
   means for driving select probe drive elements with a plurality of select frequencies;
   means for automatically scanning in a vicinity of the surface to synchronously acquire discrete scan responsive measurement signals from each probe sense element of the plurality;
   means for responsively multiplexing measurement signals onto a predetermined number of independent data channels in order to collect a corresponding plurality of measurement signals for parallel processing;
   means for demodulating each signal of the plurality against a reference frequency in order to obtain a corresponding pair of basis components for image processing;

means for converting each component pair into digital format;

automated means for storing the digital components; and means for automated parallel image processing of the digital components.

8. Apparatus according to claim 7 wherein means for providing plural frequency drives to drive elements are the same means for multiplexing sense element signals.

9. Apparatus according to claim 7 wherein said plurality of reflectance mode probes are sufficiently disposed to accommodate inspection of said surface in a single scan.

10. Apparatus according to claim 7 wherein said plurality of reflectance mode probes comprise a spatially correlated array.

11. Apparatus according to claim 10 wherein sensing elements of said probes are serially connected.

12. Apparatus according to claim 10 wherein said array is fabricated to be a flexible, integrated probe array capable of conforming to accommodate complex surface geometries.

* * * * *